United States Patent
Zhang (10) Patent No.: US 10,638,842 B2
(45) Date of Patent: May 5, 2020

(54) SMART SEAT AND CONTROL METHOD FOR THE SAME

(71) Applicant: BOE TECHNOLOGY GROUP CO., LTD., Beijing (CN)

(72) Inventor: Ying Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/941,938

(22) Filed: Mar. 30, 2018

(65) Prior Publication Data
US 2019/0059589 A1 Feb. 28, 2019

(30) Foreign Application Priority Data
Aug. 28, 2017 (CN) .......................... 2017 1 0755549

(51) Int. Cl.
*A47C 1/024* (2006.01)
*A47C 1/034* (2006.01)
(Continued)

(52) U.S. Cl.
CPC ............ *A47C 1/024* (2013.01); *A47C 1/0342* (2013.01); *A47C 7/72* (2013.01); *A47C 17/16* (2013.01);
(Continued)

(58) Field of Classification Search
CPC .. A47C 1/024; A47C 1/034; B60N 2002/0268
See application file for complete search history.

(56) References Cited

U.S. PATENT DOCUMENTS 6,526,643 B1 * 3/2003 Renault ................ B60N 2/0244
29/407.05
9,082,239 B2 * 7/2015 Ricci ........................ B60Q 1/00
(Continued)

FOREIGN PATENT DOCUMENTS

CN 204536280 U 8/2015
CN 204654331 U 9/2015
(Continued)

OTHER PUBLICATIONS

Office Action received for Chinese Patent Application No. 201710755549.5, dated Apr. 22, 2019, 22 pages (12 pages of English Translation and 10 pages of Original Office Action).
(Continued)

*Primary Examiner* — Timothy J Brindley
(74) *Attorney, Agent, or Firm* — Womble Bond Dickinson (US) LLP (57) ABSTRACT

The embodiments of the invention provide a smart seat and a control method for the same, which smart seat includes a seat body, a vital sign detector and a controller. The seat body includes a backrest, a seating surface and a backrest driver for driving the backrest to make an open and close movement relative to the seating surface. The vital sign detector is used for detecting a vital sign of a user to obtain vital sign data. The controller is electrically connected with the backrest driver and the vital sign detector, respectively, determines that the user is in the sleeping state or the waking state according to the vital sign data of the vital sign detector, and controls the backrest driver to drive the open and close movement of the backrest relative to the seating surface according to the state of the user.

12 Claims, 6 Drawing Sheets

(51) Int. Cl.
    *A61B 5/00*     (2006.01)
    *A61B 8/00*     (2006.01)
    *H04N 5/225*     (2006.01)
    *A61B 8/08*     (2006.01)
    *A47C 17/16*     (2006.01)
    *A47C 7/72*     (2006.01)
    *A61B 5/08*     (2006.01)

(52) U.S. Cl.
    CPC .......... *A61B 5/4809* (2013.01); *A61B 5/6891* (2013.01); *A61B 8/08* (2013.01); *A61B 8/4209* (2013.01); *A61B 8/44* (2013.01); *A61B 8/5223* (2013.01); *H04N 5/225* (2013.01); *A61B 5/0816* (2013.01)

(56) References Cited

U.S. PATENT DOCUMENTS

| | | | |
|---|---|---|---|
| 9,290,146 B2 * | 3/2016 | Breed | B60R 21/01536 |
| 10,004,873 B1 * | 6/2018 | Hur | B60W 30/00 |
| 2014/0309891 A1 * | 10/2014 | Ricci | H04W 4/21 |
| | | | 701/48 |
| 2014/0375087 A1 * | 12/2014 | Kuno | B60N 2/22 |
| | | | 297/69 |
| 2015/0375865 A1 * | 12/2015 | Fischer | B60N 2/919 |
| | | | 701/49 |
| 2016/0046294 A1 * | 2/2016 | Lee | B60W 40/08 |
| | | | 340/576 |
| 2016/0176409 A1 * | 6/2016 | Kirsch | B60W 40/08 |
| | | | 701/37 |
| 2017/0073074 A1 * | 3/2017 | Gagnon | B64D 11/00 |
| 2017/0101032 A1 * | 4/2017 | Sugioka | B60N 2/763 |
| 2018/0065642 A1 * | 3/2018 | Frye | B60W 40/08 |
| 2018/0181919 A1 * | 6/2018 | Jobling | G06Q 10/025 |
| 2018/0222490 A1 * | 8/2018 | Ishihara | B60W 50/14 |
| 2018/0244174 A1 * | 8/2018 | Tan | B60N 2/0244 |

FOREIGN PATENT DOCUMENTS

| | | |
|---|---|---|
| CN | 205964014 U | 2/2017 |
| CN | 106667116 A | 5/2017 |
| CN | 107041730 A | 8/2017 |
| JP | 2018079840 A * | 5/2018 |

OTHER PUBLICATIONS

Office Action received for Chinese Patent Application No. 201710755549.5, dated Sep. 29, 2019, 26 pages (14 pages of English Translation and 12 pages of Office Action).

* cited by examiner

| Control the backrest to be in the close state relative to the seating surface in a case in which it is detected that the pressure value born on the seating surface is less than a preset threshold | S201 |

SMART SEAT AND CONTROL METHOD FOR THE SAME

RELATED APPLICATIONS

This application claims the benefit of Chinese patent application No. 201710755549.5 filed on Aug. 28, 2017, the entire disclosure of which is incorporated herein by reference.

TECHNICAL FIELD

The invention relates to the field of smart device technology, and in particular, to a smart seat and a control method for the same.

BACKGROUND

The pace of life in modern society is fast, the work pressure is great, and after a day of stressful work, many young people will choose is to watch TV in their seats or on the sofa as a relaxing rest when they return home. In the state of brain relaxation, it is easy to sit and fall asleep, and due to age and lack of energy, it is also easy for a lot of elderly people to nap or fall asleep in the leisure activities of sitting and watching TV or listening to the radio. When an adult falls asleep in the state of sitting posture, it is very easy to cause muscle strain since a twisted posture is maintained for a long time. Meanwhile, the state of sitting and falling asleep is also not conducive to blood supply to the heart and blood circulation throughout the body, head droop will increase respiratory resistance, and when he wakes up after sitting and falling asleep for some time, the sense of physical fatigue will be more aggravated, the whole body ache results, and even for some elderly people with cardiovascular and cerebrovascular diseases, fatal accidents may further occur during sleep.

Existing seats can usually only cause users to stretch their bodies as much as possible when seated in the seats to improve comfort by increasing the angles between the backrests of the seats and the seating surfaces of the seats or improving the elasticity of the backrests and the surfaces of the seats. However, when a user is in an asleep state, since his upper body is still in a posture of sitting up, and natural relaxation when he is asleep will make the upper body curl up, his head will droop due to gravity and oppress the trachea, leading to that the blood supply to the heart and the respiratory circulation throughout the body are subject to to greater resistance, and yet it is difficult to alleviate the forced tension or twisting force of the muscles of the upper body only by the elasticity of the seat surface material.

Since the existing seats partially promote the posture comfort of users in a waking state, it is easier for a situation in which a user sits and falls asleep in the seat to happen. However, when the situation in which a user sits and falls asleep in the seat happens, a poor sleep posture will still adversely affect the user's body.

SUMMARY

An aspect of an embodiment of the invention provides a smart seat including a seat body, a vital sign detector and a controller. The seat body includes a backrest, a seating surface and a backrest driver for driving the backrest to make an open and close movement relative to the seating surface. The vital sign detector is used for detecting a vital sign of a user to obtain vital sign data. The controller is electrically connected with the backrest driver and the vital sign detector, respectively, determines that the user is in the sleeping state or the waking state according to the vital sign data of the vital sign detector, and controls the backrest driver to drive the open and close movement of the backrest relative to the seating surface according to the state of the user.

In an example, the backrest is hinged with the seating surface by a side, and the backrest driver drives the backrest to make the open and close movement relative to the seating surface with its hinging side as the axis.

In an example, the controller controls the backrest to change to the open state in a case in which the controller determines that the user is in the sleeping state according to the vital sign data.

Further, the smart seat of an embodiment of the invention further includes a pressure sensor which is arranged on the seating surface and electrically connected with the controller, and the controller is used for controlling the backrest to be in the close state in a case in which the pressure value born on the seating surface detected by the pressure sensor is less than a preset threshold.

In an example, the vital sign detector is an ultrasonic detector and a processing module, the ultrasonic detector is arranged on the front side of the seat body and sends an ultrasonic signal toward the direction of the seat body and receives it, the processing module determines the user's respiratory frequency and/or degree of chest undulation according to the information of the ultrasonic signal received by the ultrasonic detector, and the controller determines that the user is in the sleeping state or the waking state according to the user's respiratory frequency and/or degree of chest undulation.

Further, the seat body further includes a leg supporting plate mutually hinged with the seating surface by a side and a leg supporting plate driver arranged between the seating surface and the leg supporting plate, and the leg supporting plate driver is electrically connected with the controller and used for driving the leg supporting plate to make an open and close movement relative to the seating surface with its hinging side as the axis under the control of the controller.

In an example, on the backrest is further arranged a supporting piece which is used for fixing the relative position between the backrest and the seating surface.

Further, the smart seat of an embodiment of the invention further includes at least one vibration sensor, the vibration sensor is arranged on the seating surface and electrically connected with the controller, and the controller is used for driving the vital sign detector to detect a vital sign of the user in a case in which the vibration state value on the seating surface which is detected by the vibration sensor in a preset period of time is less than a preset threshold.

In an example, on the ultrasonic detector is further arranged an alignment camera which is electrically connected with the controller, on the seat body is further arranged an alignment mark, and the alignment camera is used for capturing an image of the alignment mark, in order that the controller regulates the orientation direction in which the ultrasonic detector sends the ultrasonic signal according to the image of the alignment mark.

Further, on the seat body is further arranged a control button which is electrically connected with the controller and used for controlling the backrest driver to drive the open and close movement of the backrest relative to the seating surface after the control button is triggered.

Another aspect of an embodiment of the invention provides a control method for a smart seat including a backrest, a seating surface and a backrest driver for driving the backrest to make an open and close movement relative to the seating surface. The control method includes: obtaining vital sign data by detecting a vital sign of a user located in the smart seat, determining that the user is in the sleeping state or the waking state according to the vital sign data, and controlling the backrest driver to drive the backrest to make the open and close movement relative to the seating surface according to the state of the user.

Further, the control method further includes: controlling the backrest to be in the close state in a case in which it is detected that the pressure value born on the seating surface is less than a preset threshold.

In an example, the obtaining vital sign data by detecting a vital sign of a user located in the smart seat and determining that the user is in the sleeping state or the waking state according to the vital sign data includes: with a preset period of time as a cycle, circularly sending an ultrasonic signal toward the user and receiving it, to obtain the information of the ultrasonic signal, determining the user's respiratory frequency and/or degree of chest undulation according to the information of the ultrasonic signal, and comparing the user's respiratory frequency and/or degree of chest undulation with a reference value of the user in the waking state, to determine that the user is in the sleeping state or the waking state.

Further, the control method further includes: with a preset period of time as a cycle, obtaining the vibration state value on the seating surface, and when the vibration state value is less than a preset threshold in the preset period of time, obtaining vital sign data by detecting the vital sign of the user located in the smart seat and determining that the user is in the sleeping state or the waking state according to the vital sign data.

Further, on the seat body is further arranged a control button, and the control method further includes: obtaining a trigger signal of the control button, and controlling the backrest driver to drive the backrest to make the open and close movement relative to the seating surface according to the trigger signal of the control button.

The embodiments of the invention provide a smart seat and a control method for the same, which includes a seat body, a sleep detector and a controller. The seat body includes a backrest, a seating surface and a backrest driver for driving the backrest to make an open and close movement relative to the seating surface. The vital sign detector is used for detecting a vital sign of a user to obtain vital sign data. The controller is electrically connected with the backrest driver and the vital sign detector, respectively, determines that the user is in the sleeping state or the waking state according to the vital sign data of the vital sign detector, and controls the backrest driver to drive the open and close movement of the backrest relative to the seating surface according to the state of the user. The vital sign of the user is detected by the vital sign detector, and it is judged in the controller whether the user is in the sleeping state or in the waking state. When it is determined that the user has already been in the sleeping state, the controller controls the backrest driver to drive the backrest to make the open and close movement relative to the seating surface, which enables the user to change from a sitting posture to a lying posture with the open and close movement of the backrest in the sleeping state.

BRIEF DESCRIPTION OF THE DRAWINGS

In order to more clearly illustrate the technical solutions in embodiments of the invention or the prior art, the appended drawings needing to be used in the description of the embodiments or the prior art will be introduced briefly in the following. Obviously, the drawings in the following description are only some embodiments of the invention, and for the person having ordinary skills in the art, other drawings may also be obtained according to these drawings under the premise of not paying out undue experimentation.

DETAILED DESCRIPTION OF THE INVENTION

In the following the technical solutions in embodiments of the invention will be described clearly and completely in connection with the drawings in the embodiments of the invention. Obviously, the described embodiments are just a part of the embodiments of the invention, and not all the embodiments. Based on the embodiments in the invention, all the other embodiments obtained by the person having ordinary skills in the art under the premise of not paying out undue experimentation pertain to the scope protected by the invention.

REFERENCE SIGNS

10 Seat body
11 Backrest
110 Supporting piece
12 Seating surface
13 Backrest driver
14 Leg supporting plate
15 Leg supporting plate driver
16 Foot supporting plate 17 Foot supporting plate driver
18 Control button
20 Vital sign detector
21 Ultrasonic detector
22 Processing module
23 Alignment camera
24 Alignment mark
30 Controller
40 Pressure sensor
50 Vibration sensor.

Figure 1:
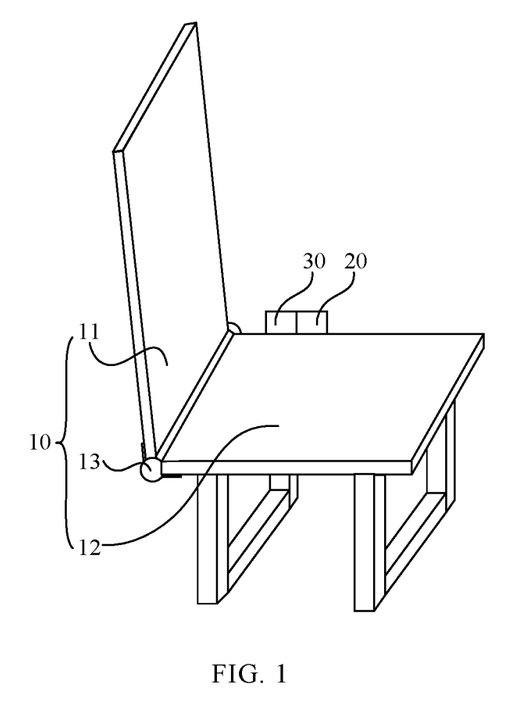
FIG. 1 is the close state of a structure diagram of a smart seat provided by an embodiment of the invention.

An embodiment of the invention provides a smart seat, which, as shown in FIG. 1, includes a seat body 10, a vital sign detector 20 and a controller 30. The seat body 10 includes a backrest 11, a seating surface 12 and a backrest driver 13 for driving the backrest 11 to make an open and close movement relative to the seating surface 12. The vital sign detector 20 is used for detecting a vital sign of a user to obtain vital sign data. The controller 30 is electrically connected with the backrest driver 13 and the vital sign detector 20, respectively, determines that the user is in the sleeping state or the waking state according to the vital sign data of the vital sign detector 20, and controls the backrest driver 13 to drive the open and close movement of the backrest relative to the seating surface 12 according to the state of the user.

It needs to be noted that, firstly, as shown in FIG. 1, for the seat body 10 including the backrest 11, the seating surface 12 and the backrest driver 13 in the embodiment of the invention, the arrangement relationship between its components is just a conventional arrangement relationship of the existing seat. Exemplarily, the backrest 11 is just the part for the user's upper body to abut against, and the seating surface 13 is just the part that contacts the user's hip when the user uses it in a sitting posture and is used for bearing the gravity of the user in the state of sitting posture. Therein, since the smart seat of the embodiment of the invention can drive the backrest 11 to be in the open state, namely, cause the user to lie on the smart seat in the open state, under the control of the controller 30, the backrest 11 of the embodiment of the invention needs to include a part capable of supporting the head of the user.

Secondly, the backrest driver 13 is used for driving the backrest 11 to make the open and close movement relative to the seating surface 12, and the connection mode between the backrest 11 and the seating surface 12 will not be defined in the embodiment of the invention, as long as it can be ensured that the backrest 11 can make the open and close movement relative to the seating surface under the drive of the backrest driver 13. Therein, the specific structure of the backrest driver 13 will also not be defined. In an example, an electrode is arranged as the backrest driver 13 to drive the open and close movement between the backrest 11 and the seating surface 12, which can reduce the problems of the movement stability of the smart seat of the embodiment of the invention at the time of the open and close movement and the phased jam in the movement process.

Thirdly, the angle of the open and close movement will not be defined in the embodiment of the invention, and there at least include two states, the close state and the open state, between the backrest 11 and the seating surface 12. When the backrest 11 and the seating surface 12 are in the close state, namely, the state in which the user is in the sitting posture, it may be considered approximately that in the close state the angle between the backrest 11 and the seating surface 12 is 90°, but it is not limited thereto. For example, to enable the user's upper body to rest on the backrest 11 for a rest in the state of sitting posture, the angle between the backrest 11 and the seating surface 12 in the close state may also be set to 90° or other angles. Likewise, when the backrest 11 and the seating surface 12 are in the open state, namely, the state in which the user is in the lying posture, it may be considered approximately that in the open state the angle between the backrest 11 and the seating surface 12 is 180°, but it is also not limited thereto. For another example, it may also be such that when the user is in the state of lying posture, the angle between the backrest and the seating surface 12 is 170° or set to other angles according to other specific requirements.

Fourthly, the vital sign detector 20 detects vital sign data of the user. Vital signs include indicative data reflecting the state of human life such as the pulse, the respiration, the body temperature, the blood pressure, etc. The smart seat of the embodiment of the invention needs to detect whether the user using the smart seat is in the waking state or the sleeping state. Therefore, the vital sign data described in the embodiment of the invention is one that can embody different data ranges in the person's waking state and sleeping state, for example, the pulse, the respiration.

Fifthly, the controller 30 judges whether the state of the user is in the sleeping state or in the waking state according to the vital sign data detected by the vital sign detector 20, and controls the backrest driver 13 to drive the backrest 11 to make the open and close movement relative to the seating surface 12 to correspondingly adjust the open and close state of the smart seat of the embodiment of the invention by the electrical connection (the connection line is not shown in FIG. 1, the same as below) between it and the backrest driver 13 according to the current state of the user. For example, when it is determined that the user is in the sleeping state, it controls the backrest driver 13, such that there is the open state between the backrest 11 and the seating surface 12, causing the user to change to the lying posture for a comfortable rest. For another example, when it is detected that the user changes from the sleeping state to the waking state, it may further control the backrest driver 13, to cause the backrest 11 and the seating surface 12 to be in the close state and cause the user to change to the sitting posture.

Sixthly, in the embodiment of the invention, the controller 30 determines the current state of the user. Since when the user is in the sleeping state and in the waking state, there is a difference between his vital sign data, for example, the respiratory frequency of a person in the waking state is higher as compared to that in the sleeping state, a threshold range of the vital sign data corresponding to the sleeping state or waking state may be preset in the controller 30, in order that the controller 30 judges the current state of the user by comparing the current detection data with the preset threshold range of the data. Therein, the preset threshold range of the vital sign data corresponding to the sleeping state or waking state may be empirical values obtained by the person having ordinary skills in the art after a large sample experiment, may be obtained by calculation according to a corresponding calculation formula, or also may be obtained by the person having ordinary skills in the art in other ways, which will not be specifically defined by the embodiment of the invention.

The vital sign of the user is detected by the vital sign detector, and it is judged in the controller whether the user is in the sleeping state or in the waking state. When it is determined that the user has already been in the sleeping state, the controller controls the backrest driver to drive the backrest to make the open and close movement relative to the seating surface, which enables the user to change from a sitting posture to a lying posture with the open and close movement of the backrest in the sleeping state. This may alleviate the problems of muscle tension, poor breathing and insufficient blood supply to the heart that easily take place when sleeping in the sitting posture, and improve the comfort in using the smart seat when sleeping.

In an example, as shown in FIG. 1, the backrest 11 is hinged with the seating surface 12 by a side, and the backrest driver 13 drives the backrest 11 to make the open and close movement relative to the seating surface 12 along its hinging side.

The backrest 11 and the seating surface 12 are hinge connected by a side, which, when the open and close movement is made between the backrest 11 and the seating surface 12 along the hinging side thereof, can cause the movement trajectory of the backrest 11 to be stable and the movement process to be smooth, and in the process of driving the backrest 11 to move with the hinging side as the axis by the backrest driver 13, can cause the user's upper body to move at a constant speed with the backrest 11 as much as possible when he changes from the sitting posture to the lying posture, reduce the vibration and jam that may happen in this process, and improve the comfort in using the smart seat of the embodiment of the invention.

In an example, the controller 30 controls the backrest 11 to change to the open state in a case in which the controller 30 determines that the user is in the sleeping state according to the vital sign data.

Figure 2:
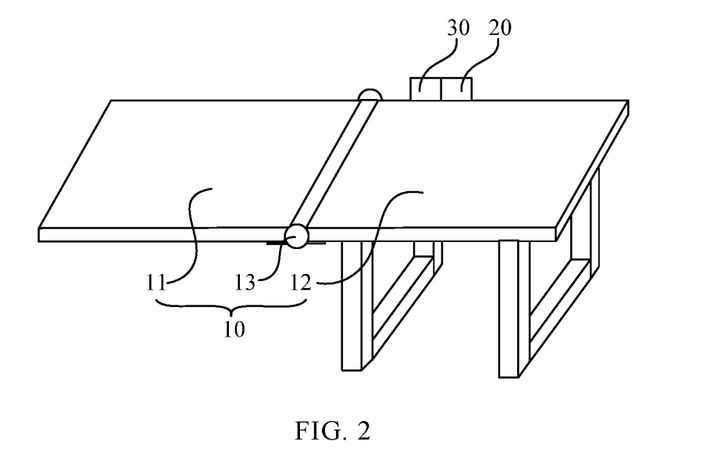
FIG. 2 is the open state of a structure diagram of a smart seat provided by an embodiment of the invention.

Generally, for the smart seat of the embodiment of the invention, initially, as shown in FIG. 1, the backrest 11 and the seating surface 12 are in the close state. The user only uses the smart seat for rest in the sitting posture in the waking state. According to detection of the user's vital sign data by the vital sign detector 20, judgment is made in the controller 30. In a case in which it is determined that the user has already the sleeping state, the controller 30 controls the backrest driver 13 to drive the backrest 11 to change to the open state, which, as shown in FIG. 2, can cause the user to convert from the sitting posture to the lying posture in the sleeping state, and enable the user to fully relax his body without disturbing the user's sleep.

Figure 3:
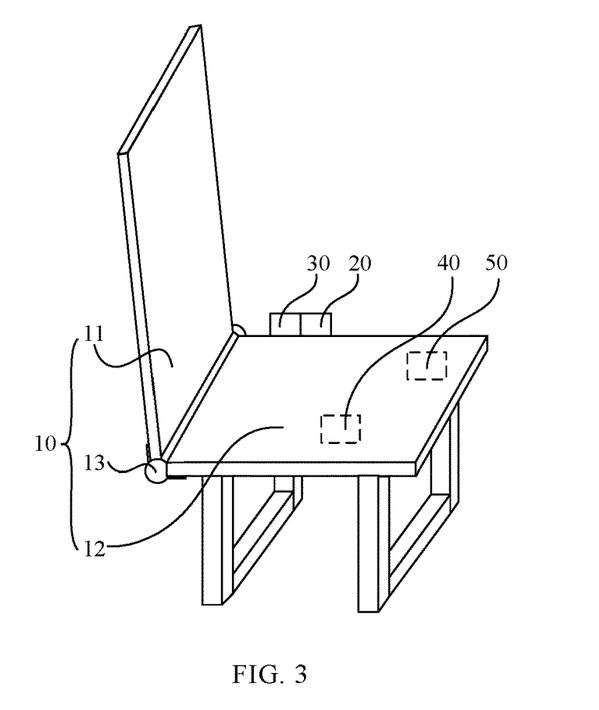
FIG. 3 is a structure diagram of a smart seat provided by an embodiment of the invention which further includes a pressure sensor.

Further, as shown in FIG. 3, the smart seat of an embodiment of the invention further includes a pressure sensor 40 which is arranged on the seating surface 12 and electrically connected with the controller 30, and the controller 30 is used for controlling the backrest 11 to be in the close state in a case in which the pressure value born on the seating surface 12 detected by the pressure sensor 40 is less than a preset threshold.

It needs to be noted that, the pressure sensor 40 is used for detecting the pressure on the seating surface 12, and the embodiment of the invention will not define the arrangement position and the arrangement number of the pressure sensor 40, as long as the pressure value on the seating surface 12 can be obtained. To guarantee the comfort in using the seating surface 12 and avoid occurrence of a case in which the surface of the seating surface 12 is uneven, generally, the pressure sensor 40 will not be arranged on a surface of the seating surface 12 which is in direct contact with the user. For example, to improve the surface softness of the smart seat of the embodiment of the invention, on the surface of the seat body may further be included a sponge, wrap cloth, etc., and the pressure sensor 40 may be arranged under the sponge, and the wrap cloth.

As shown in FIG. 3, in the smart seat of the embodiment of the invention, the pressure sensor 40 detects the pressure value to which the seating surface 12 is subject, and the controller 30 compares the pressure value detected by the pressure sensor 40 with the preset threshold, and judges whether there is a person in the smart seat of the embodiment of the invention. For example, if the range of the preset threshold is set to be 0~2 kg, then when the pressure value perceived by the pressure sensor 40 on the seating surface 12 is less than 2 kg, the controller 30 judges that the smart seat is in a state of being unoccupied by comparison and controls the backrest 11 to be in the close state. Therein, controlling the backrest 11 to be in the close state includes two situations. The first situation is that in the current state, the smart seat is in the open state, that is, after the controller 30 controls the backrest driver 13 to drive the backrest 11 to change to the open state relative to the seating surface 12 in the case in which the vital sign detector 20 detects the user's vital sign data and it is judged in the controller 30 to determine that the user has already entered the sleeping state, the controller 30 controls the backrest driver 13 to drive the backrest 11 to be closed relative to the seating surface 12 according to the judgment result that the smart seat is unoccupied. The second situation is that in the current state, the smart seat is just in the close state, and then when it is judged that the smart seat is unoccupied, the controller 30 learns that the state of the seat body 10 is the close state and will not send a driving instruction, and it suffices to keep the close state. As such, when the smart seat of the embodiment of the invention is in the unoccupied state, the smart seat is restored to the initial close state, which facilitates the user to be able to directly use it the next time on the one hand, and can also save space on the other hand.

Figure 4:
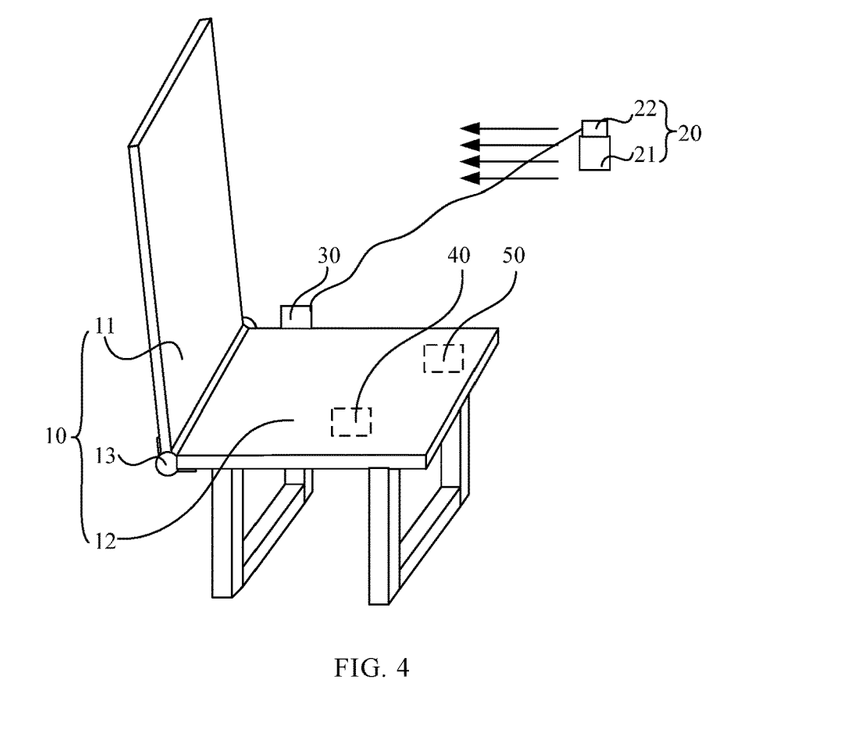
FIG. 4 is a structure diagram of a smart seat provided by an embodiment of the invention in which the vital sign detection is an ultrasonic detector and a processing module.

In an example, as shown in FIG. 4, the vital sign detector 20 is an ultrasonic detector 21 and a processing module 22, the ultrasonic detector 21 is arranged on the front side of the seat body 10 and sends an ultrasonic signal toward the direction of the seat body 10 and receives it, the processing module 22 determines the user's respiratory frequency and/or degree of chest undulation according to the information of the ultrasonic signal received by the ultrasonic detector 21, and the controller 30 determines that the user is in the sleeping state or the waking state according to the user's respiratory frequency and/or degree of chest undulation.

When a person breathes, the lungs will expand and contract with it due to inhalation and exhalation, it can be seen from the appearance that the chest of the person will undulate with his respiration, and if an ultrasonic signal is sent toward the chest and abdomen position of the human body, and arithmetic processing is performed on the received ultrasonic signal according to the Doppler effect, the user's respiratory frequency may be obtained. According to the difference in time between sending and receiving the ultrasonic signal and the degree of attenuation of the intensity of the ultrasonic signal, the distance over which the signal is sent may be obtained, that is, the user's degree of chest undulation may be obtained by calculation.

As shown in FIG. 4, the vital sign detector 20 includes an ultrasonic detector 21 and a processing module 22, and by the ultrasonic detector 21 sending a signal toward the user and receiving it and by processing the received signal in the processing module 22, the user's respiratory frequency and/or degree of chest undulation is obtained. When the vital sign detector 20 includes an ultrasonic detector 21 and a processing module 22, the ultrasonic detector 21 needs to be arranged on the front side of the seat body 10 as shown in FIG. 4, and send an ultrasonic signal toward the direction of the seat body 10 as shown by the arrows in FIG. 4. In particular, the ultrasonic detector 21 sends an ultrasonic signal, the sent ultrasonic signal arrives at the user along the sending direction, returns and is received, and the received ultrasonic signal is processed and calculated in the processor. Since the respiratory frequency of a person will slow down in the sleeping state and the degree of chest undulation will also decrease accordingly, by the ultrasonic detector 21 continuously sending an ultrasonic signal toward the user and receiving it, in an example, sending an ultrasonic signal toward the user's chest position and receiving it, the user's respiratory frequency and/or degree of chest undulation may be obtained according to the calculation and processing of the processing module 22, and then it is determined by the controller 30 that the user is in the sleeping state or the waking state.

As compared to use of a contact-type vital sign detector, by using the ultrasonic detector 21 and the processing module 22 as the vital sign detector 20, a tedious wearing process is not needed each time the user uses it, no effect will be caused on the user's work, study and leisure & entertainment, etc. in the smart seat of the embodiment of the invention, and the accuracy of the ultrasonic detection is high.

It further needs to be noted that the vital sign detector 20 may be connected with the controller via a wire as shown in FIG. 4, or also may implement a signal connection with the controller in a wireless way. In addition, when the smart seat of the embodiment of the invention is used in a home environment and its placement position is not frequently moved, the vital sign detector 20 may be fixedly arranged at a fixed position on the front side of the seat body 10, which will not be defined by the embodiment of the invention, as long as it is ensured that the ultrasonic detector 21 sends an ultrasonic signal toward the direction of the seat body 10, and signal transmission may be implemented between the vital sign detector 20 and the controller 30.

Figure 5:
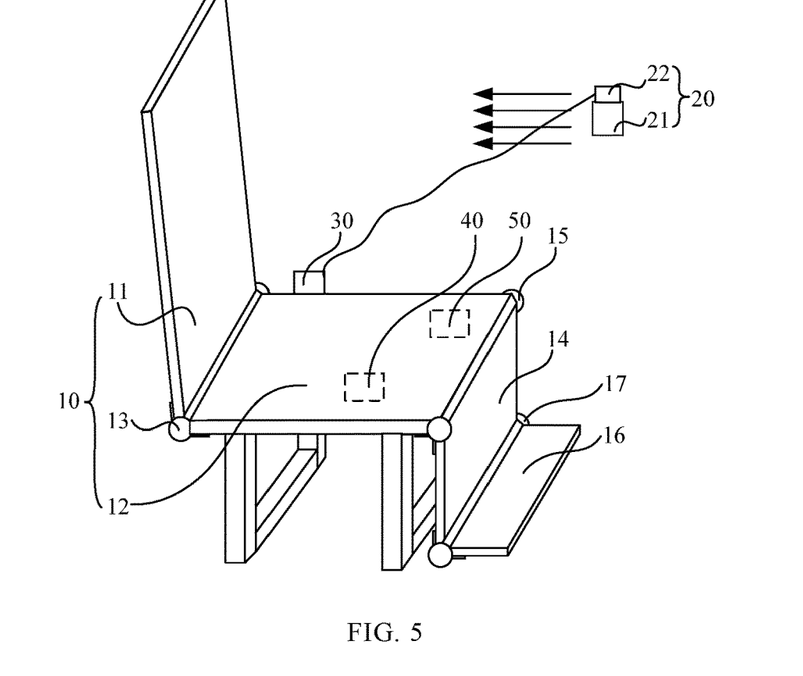
FIG. 5 is a structure diagram of a smart seat provided by an embodiment of the invention which further includes a leg supporting plate.

Further, as shown in FIG. 5, the seat body 10 further includes a leg supporting plate 14 mutually hinged with the seating surface 12 by a side and a leg supporting plate driver 15 arranged between the seating surface 12 and the leg supporting plate 14, and the leg supporting plate driver 15 is electrically connected with the controller 30 and used for driving the leg supporting plate 14 to make an open and close movement relative to the seating surface 12 with its hinging side as the axis under the control of the controller 30.

As such, as shown in FIG. 5, the seat body 10 further includes a leg supporting plate 14 mutually hinged with the seating surface 12 on a side, which plate is used for limiting the leg of a user who uses the smart seat of the embodiment of the invention and is in the sitting posture when the smart seat is in the close state, and further includes a leg supporting plate driver 15 capable of driving the leg supporting plate 14 to make the open and close movement along its hinging side, for supporting the leg of a user who uses the smart seat of the embodiment of the invention and is in the lying posture when the smart seat is in the open state. Therein, the way in which the leg supporting plate driver 15 fixes the leg supporting plate 14 and controls the open and close movement of the leg supporting plate 14 relative to the seating surface 12 is the same as that in which the backrest driver 13 fixes the backrest 11 and controls the open and close movement of the backrest 11 relative to the seating surface 12, which will not be repeated here any longer.

Likewise, as shown in FIG. 5, to further improve the comfort of user experience, the seat body 10 further includes a foot supporting plate 16 mutually hinged with the leg supporting plate 14 by a side and a foot supporting plate driver 17 arranged between the leg supporting plate 14 and the foot supporting plate 16, and the foot supporting plate driver 17 is electrically connected with the controller 30 and used for driving the foot supporting plate 16 to make an open and close movement relative to the leg supporting plate 14 with its hinging side as the axis under the control of the controller 30.

Therein, as shown in FIG. 5, the way in which the foot supporting plate driver 17 fixes the foot supporting plate 16 and controls the open and close movement of the foot supporting plate 16 relative to the leg supporting plate 14 is the same as that in which the backrest driver 13 fixes the backrest 11 and controls the open and close movement of the backrest 11 relative to the seating surface 12, which will not be repeated here any longer.

Figure 6:
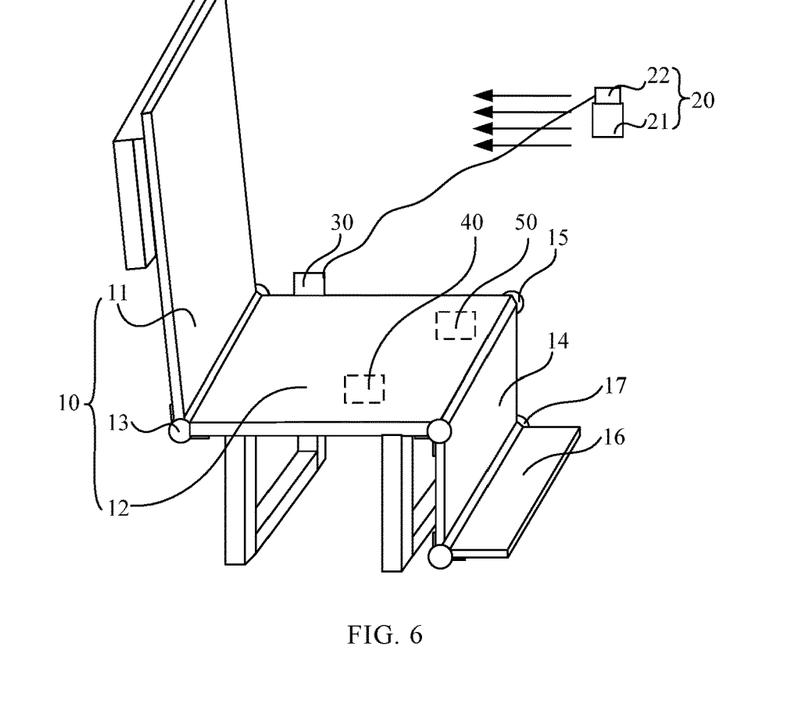
FIG. 6 is a structure diagram of the close state of a smart seat provided by an embodiment of the invention in which on the backrest is further arranged a supporting piece.

In an example, as shown in FIG. 6, on the backrest 11 is further arranged a supporting piece 110 which is used for fixing the relative position between the backrest 11 and the seating surface 12.

Figure 7:
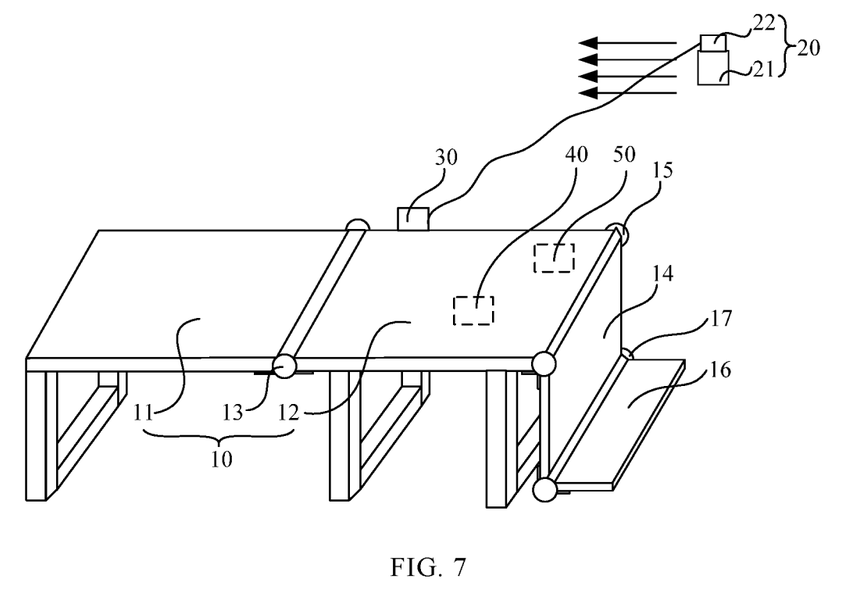
FIG. 7 is a structure diagram of the open state of a smart seat provided by an embodiment of the invention in which on the backrest is further arranged a supporting piece.

As shown in FIG. 6, when the smart seat of the embodiment of the invention is in the close state, the supporting piece 110 is retracted on the back of the backrest 11 and parallel to and/or closely clings to the back, which avoids occupying excessive too much indoor space. When the smart seat of the embodiment of the invention changes to be in the open state, i.e., perpendicular to or substantially perpendicular to the back, as shown in FIG. 7, the supporting piece 110 can be opened and abut the ground (or other supporting planes) to support the backrest 11, so as to guarantee a stable support of the weight of the user's upper body by the backrest 11 when the user is in the lying posture and avoid shaking. Exemplarily, the supporting piece 110 may be connected with the back of the backrest 11 by way of a hinge (the hinge connection is not shown in FIG. 6 and FIG. 7). Moreover, the supporting piece 110 may be expanded and retracted manually, or also may be connected with a corresponding driver (the driver for driving the supporting piece 110 is not shown in FIG. 6 and FIG. 7), and the corresponding driver is electrically connected with the controller 30, and is controlled by the controller 30 to drive the expansion and retraction of the supporting piece 110.

It needs to be noted that, when the smart seat of the embodiment of the invention includes a leg supporting plate 14 mutually hinged with the seating surface 12 by a side and a leg supporting plate driver 15 arranged between the seating surface 12 and the leg supporting plate 14, and further includes a foot supporting plate 16 mutually hinged with the leg supporting plate 14 by a side and a foot supporting plate driver 17 arranged between the leg supporting plate 14 and the foot supporting plate 16, in order to improve the fixing stability of the leg supporting plate 14 and/or the foot supporting plate 16, similar to the backrest 11, it may also be possible to arrange supporting pieces 110 (not shown in FIG. 6) on the back sides of the leg supporting plate 14 and/or the foot supporting plate 16 for supporting and fixing the leg supporting plate 14 and/or the foot supporting plate 16, respectively, when the smart seat of the embodiment of the invention is in the open state.

Further, as shown in FIG. 3, the smart seat of the embodiment of the invention further includes at least one vibration sensor 50, the vibration sensor 50 is arranged on the seating surface 12 and electrically connected with the controller 30, and the controller 30 is used for driving the vital sign detector 20 to detect a vital sign of the user in a case in which the vibration state value on the seating surface 12 which is detected by the vibration sensor 50 in a preset period of time is less than a preset threshold.

As shown in FIG. 3, the vibration sensor 50 is used for detecting the vibration on the seating surface 12. When the user uses the smart seat of the embodiment of the invention in the waking state, as a result of human physical activity, slight vibration will be transferred to the seating surface 12 and perceived by the vibration sensor 50. However, when a person is in the sleeping state, since the frequency of physical activity is reduced, it is difficult for the vibration sensor 50 to capture the vibration transferred by the user to the seating surface 12. Similar to the pressure sensor 40, in the embodiment of the invention, the arrangement position and the arrangement number of the vibration sensor 50 on the seating surface 12 will not be defined, as long as the vibration value on the seating surface 12 can be obtained. To guarantee the comfort in using the seating surface 12 and avoid occurrence of a case in which the surface of the seating surface 12 is uneven, generally, the pressure sensor 40 will not be arranged on a surface of the seating surface 12 which is in direct contact with the user.

In an example, the vibration sensor 50 may be an accelerometer or gyroscope, the two can implement detection of vibration, their installation and use is convenient, and their measurement accuracies are high.

In addition, since the user will generally not continuously perform physical activities to produce a vibration value when he is sitting in the smart seat in the waking state, the obtaining of the vibration value of the user by the vibration sensor 50 is particularly to continuously obtain it in a preset period of time. The number of times that the vibration value is obtained in the preset period of time and the amplitude of each vibration are compared with a preset threshold, and when the number of times that the vibration value is obtained in the preset period of time is lower than the minimum of the preset threshold, and/or the obtained vibration amplitudes are less than the vibration amplitude of the preset threshold, it is considered that the user may enter the sleeping state. In such a case, the controller 30 drives the vital sign detector 20 to detect the vital sign of the user. As such, it may not be necessary to cause the vital sign detector 20 to be in the state of detection and data recording and outputting in real time, which reduces the energy consumption in use of the vital sign detector 20 on the one hand, and can also decrease the amount of operation processing of the controller 30.

Figure 8:
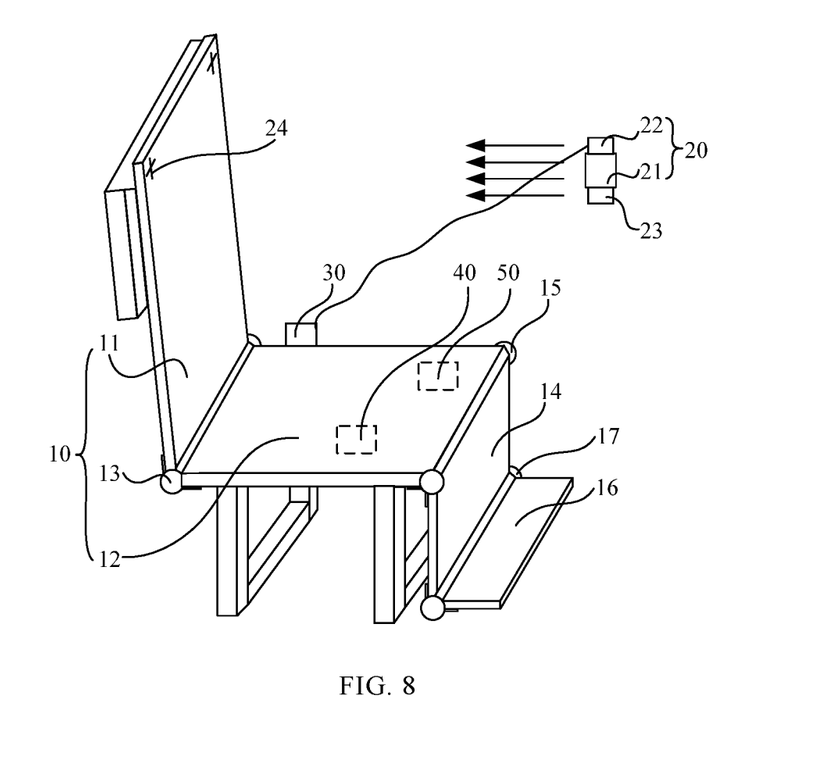
FIG. 8 is a structure diagram of a smart seat provided by an embodiment of the invention in which on the ultrasonic detector is further arranged an alignment camera.

In an example, as shown in FIG. 8, on the ultrasonic detector 21 is further arranged an alignment camera 23 which is electrically connected with the controller 30, on the seat body 10 is further arranged an alignment mark 24, and the alignment camera 23 is used for capturing an image of the alignment mark 24, in order that the controller 30 regulates the orientation direction in which the ultrasonic detector 21 sends the ultrasonic signal according to the image of the alignment mark 24.

For example, an image containing the alignment mark 24 is captured by the alignment camera 23 and is compared with the image of a preset standard position, and the orientation direction of the alignment camera 23 and the ultrasonic detector 21 or the vital sign detection 20 fixedly connected with the alignment camera 23 is regulated according to the comparison result, which enables the ultrasonic detector 21 to send an ultrasonic signal toward the center area of the seat body and receive it. That the ultrasonic detector 21 can send an ultrasonic signal toward the center area of the seat body and receive it can make the calculation of the respiratory frequency and/or degree of chest undulation of a user sitting in the seat body 10 of the embodiment of the invention more accurate.

It needs to be noted that, the shape and arrangement number of the alignment mark 24 will not be specifically defined in the embodiment of the invention, as long as it is satisfied that the alignment mark 24 is fixedly arranged at a certain position of the seat body 10 and the alignment camera can capture an image containing the alignment mark 24.

Figure 9:
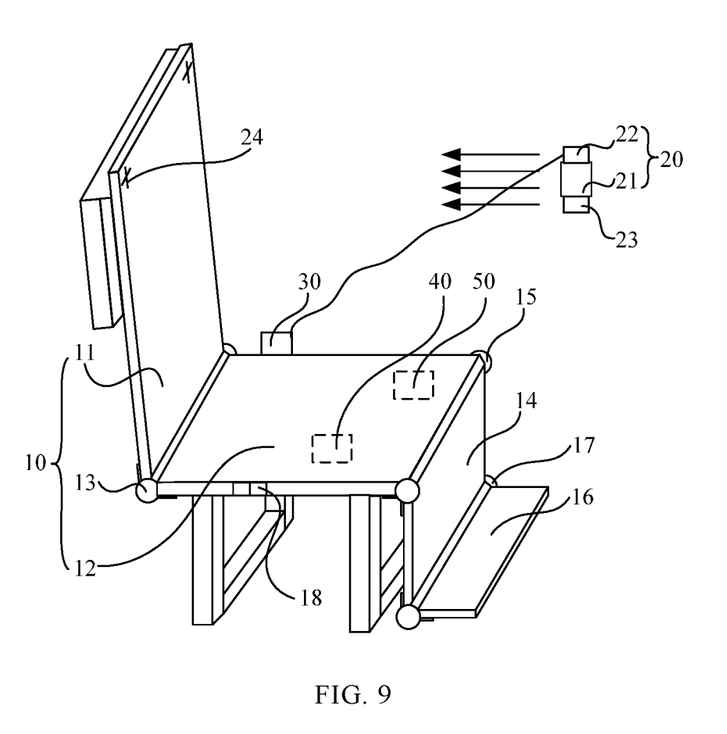
FIG. 9 is a structure diagram of a smart seat provided by an embodiment of the invention on which is further included a control button.

Further, as shown in FIG. 9, on the seat body 10 is further arranged a control button 18 which is electrically connected with the controller 30 and used for controlling the backrest driver 13 to drive the open and close movement of the backrest 11 relative to the seating surface 12 after the control button is triggered.

As shown in FIG. 9, exemplarily, on the smart seat of the embodiment of the invention are arranged control buttons 18 for performing operations of "open" and "close", the user may carry out the trigger operation of a control button 18 by pressing the control button 18 on his own as needed, and after the control button 18 is triggered, the controller 30 controls the backrest driver 13 to drive the backrest 11 to make the corresponding open and close movement relative to the seating surface 12.

It needs to be noted that, firstly, the arrangement position and the arrangement number of the control button 18 on the smart seat of the embodiment of the invention will not be specifically defined, and the arrangement position may be arranged on a side of the seating surface 12 as shown in FIG. 9, or also may be arranged on the backrest 11, or also may be separately arranged as a manual operation handle by way of a connection line or wireless connection. For the arrangement number, there may be arranged two control buttons 18 of "open" and "close" as shown in FIG. 9, which perform corresponding operations respectively when corresponding control buttons 18 are triggered. It may also be possible to only arrange one control button 18 for changing the existing state of the smart seat of the embodiment of the invention by the controller 30 when the control button 18 is triggered, for example, changing from the open state to the close state, or if the current state is the close state, changing the close state to the open state when the control button 18 is triggered.

Secondly, when the smart seat of the embodiment of the invention further includes a leg supporting plate 14 mutually hinged with the seating surface 12 by a side and a leg supporting plate driver 15 arranged between the seating surface 12 and the leg supporting plate 14, the controller 30 also controls the leg supporting plate driver 15 to drive the leg supporting plate 14 to making a corresponding open and close movement when it controls the backrest driver 13 to drive the backrest 11 to make a corresponding open and close movement after the control button 18 is triggered. Therein, the order in which the controller 30 controls the backrest driver 13 and the leg supporting plate driver 15 will not be defined, and it may control the two to make the open and close movement simultaneously, or they may also move one after another. Likewise, when the smart seat of the embodiment of the invention further includes a foot supporting plate 16 mutually hinged with the leg supporting plate 14 by a side and a foot supporting plate driver 17 arranged between the leg supporting plate 14 and the foot supporting plate 16, the controller 30 is further used for controlling the foot supporting plate driver 17 to drive the foot supporting plate 16 to making a corresponding open and close movement relative to the leg supporting plate 14 after the control button 18 is triggered. Therein, the order in which the controller 30 controls the backrest driver 13 and the leg supporting plate driver 15 will not be defined, and it may control the two to make the open and close movement relative to the seating surface 12 simultaneously, or they may also move one after another.

Figure 10:
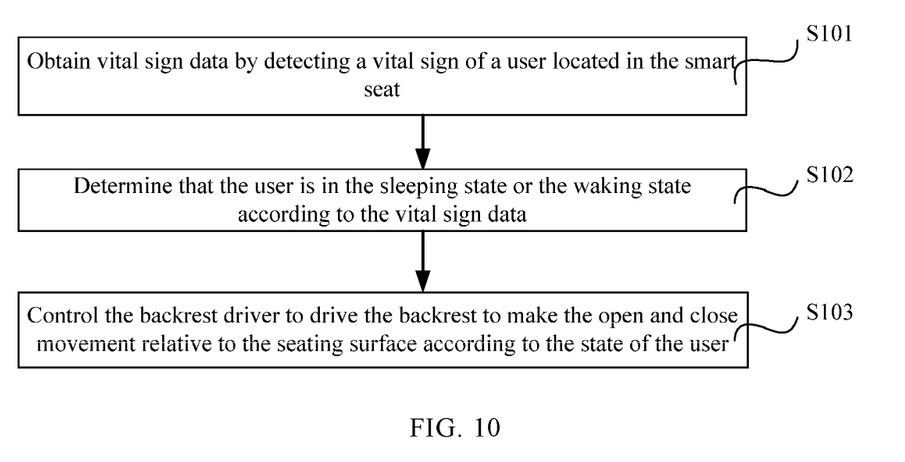
FIG. 10 is a flow chart I of a control method for a smart seat provided by an embodiment of the invention.

Another aspect of an embodiment of the invention provides a control method for a smart seat. As shown in FIG. 1, the smart seat includes a backrest 11, a seating surface 12 and a backrest driver 13 for driving the backrest 11 to make an open and close movement relative to the seating surface 12. As shown in FIG. 10, the control method includes:

S101, obtaining vital sign data by detecting a vital sign of a user located in the smart seat, S102, determining that the user is in the sleeping state or the waking state according to the vital sign data, and S103, controlling the backrest driver 13 to drive the backrest 11 to make the open and close movement relative to the seating surface 12 according to the state of the user.

As shown in FIG. 10, first, a vital sign of a user in the smart seat is detected to obtain vital sign data of the user, and by analyzing and processing the vital sign data, it can be reflected whether the user is currently in the sleeping state or in the waking state. For example, there is a significant difference in the respiratory frequency when a person is in the sleeping state and in the waking state, the respiratory frequency of the person in the waking state is higher as compared to that in the sleeping state, and it may be determined whether a user is in the sleeping state or the waking state according to the user's respiratory frequency. A threshold range of the vital sign data corresponding to the sleeping state or waking state may be preset, and the user's vital sign data is compared with the threshold range after it is obtained, so as to determine the user's current state. The preset threshold range of the vital sign data corresponding to the sleeping state or waking state may be empirical values obtained by the person having ordinary skills in the art after a large sample experiment, may be obtained by calculation according to a corresponding calculation formula, or also may be obtained by the person having ordinary skills in the art in other ways. It is determined in the above way according to the vital sign data that the user is in the sleeping state or the waking state, and according to the state of the user, the backrest driver 13 is controlled to drive the backrest 11 to make the open and close movement relative to the seating surface 12, so as to adjust the open and close state of the smart seat to match the user's current state.

In addition, since there is a certain degree of individual differences in vital sign data, an account may further be established for each user respectively, in order to further improve the accuracy of detection and reduce the possibility of misjudgment. For a user who uses the smart seat the first time, the vital sign data of at least one waking state is acquired as the threshold range for subsequent comparison, and a personal account is established for data storage. When the user uses the smart seat the next time, the user may be determined as an existing user by way of automatic match or manual selection, thereby directly invoking the existing data in his account.

Figure 11:
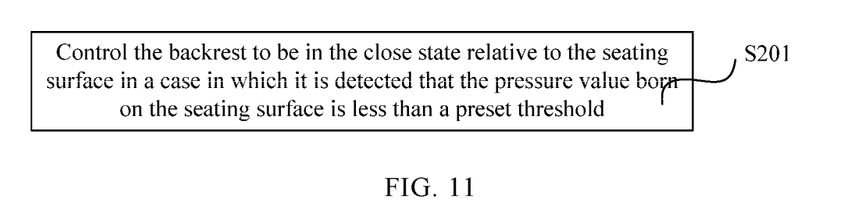
FIG. 11 is a flow chart II of a control method for a smart seat provided by an embodiment of the invention.

Further, as shown in FIG. 11, the control method further includes: S201, controlling the backrest 11 to be in the close state in a case in which it is detected that the pressure value born on the seating surface 12 is less than a preset threshold.

The preset threshold of the pressure value is preset for determining whether there is a person on the seating surface 12. Exemplarily, in general, the weight of the user will not be lower than 10 kg. Judging by weight, if the pressure value on the seating surface 12 is less than 10 kg, it is impossible that a user is using it. Therefore, the preset threshold of the pressure value may be set to be 10 kg. When the detected pressure value on the seating surface 12 is less than the preset threshold, it is considered that the smart seat of the embodiment of the invention is currently unoccupied, and the backrest 11 is controlled to be in the close state, and the initial posture of the smart seat is restored. If the smart seat itself is in the close state currently, then the current state is kept and no operation of open and close movement is performed.

Figure 12:
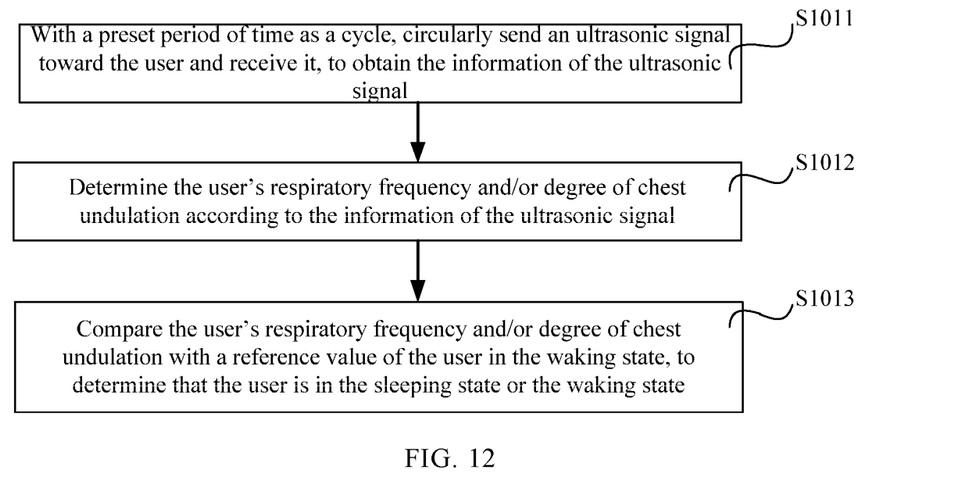
FIG. 12 is a flow chart III of a control method for a smart seat provided by an embodiment of the invention.

In an example, as shown in FIG. 12, the steps s101-S102 (obtaining vital sign data by detecting a vital sign of a user located in the smart seat, and determining that the user is in the sleeping state or the waking state according to the vital sign data) include:

S1011, with a preset period of time as a cycle, circularly sending an ultrasonic signal toward the user and receiving it, to obtain the information of the ultrasonic signal.

S1012, determining the user's respiratory frequency and/or degree of chest undulation according to the information of the ultrasonic signal.

S1013, comparing the user's respiratory frequency and/or degree of chest undulation with a reference value of the user in the waking state, to determine that the user is in the sleeping state or the waking state.

Since recording of the user's respiratory frequency requires a range of period of time, a preset period of time is set first. Since if the period of time is too short, it may be difficult to get the rule of the respiratory frequency and to compare the difference between when the user is in the sleeping state and when he is in the waking state, whereas if the period of time is too long, it may result in that the judgment operation of the smart seat is too slow, the specific time length of the preset period of time will not be defined in the embodiment of the invention. For example, it may be one minute, three minutes, etc., and it may be specifically set balancing the above two conditions according to the specific use needs.

As shown in FIG. 12, after the preset period of time is determined, the information of the ultrasonic signal is obtained circularly with the preset period of time as the cycle, wherein each set of ultrasonic signal information is the ultrasonic signal in the time length range of one preset period of time. For the received ultrasonic signal, a corresponding calculation according to the Doppler effect, for example, obtains the user's respiratory frequency, and the distance over which the signal is sent may be obtained according to the difference in time between sending and receiving and the degree of attenuation of the intensity of the ultrasonic signal. When an ultrasonic signal is sent toward the user, the user's chest will undulate in the process of breathing, and the user's degree of chest undulation may be obtained according to the calculation processing for the received ultrasonic signal. The user's respiratory frequency and/or degree of chest undulation is obtained through the above means according to the needs.

Then, the user's respiratory frequency and/or degree of chest undulation is compared with a reference value of the user in the waking state. In general, a person's breathing is relatively short when he is in the waking state, whereas after he enters the sleeping state, the respiratory frequency will slow down, and the magnitude of the chest undulation will also increase. By comparison with an acquired or stored reference value of the user's respiratory frequency and/or degree of chest undulation in the waking state, it is determined that the user has entered the sleeping state if the threshold range of the reference value of the user in the waking state is exceeded, and it is determined that the user is in the waking state if the current respiratory frequency and/or degree of chest undulation is within the threshold range of the reference value of the user in the waking state.

Likewise, for the reference value of the user in the waking state, it may be empirical values obtained by the person having ordinary skills in the art after a large sample experiment, may be obtained by calculation according to a corresponding calculation formula, or also may be obtained by the person having ordinary skills in the art in other ways, which will not be specifically defined by the embodiment of the invention.

Figure 13:
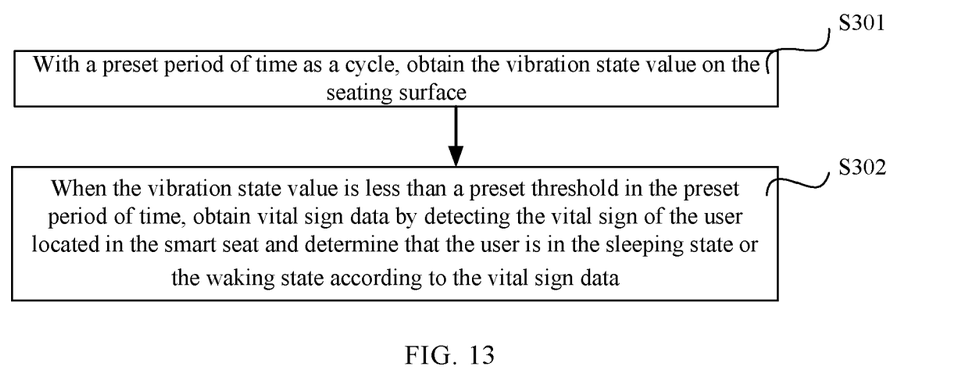
FIG. 13 is a flow chart IV of a control method for a smart seat provided by an embodiment of the invention.

Further, as shown in FIG. 13, the control method further includes:

S301, with a preset period of time as a cycle, obtaining the vibration state value on the seating surface 12.

S302, when the vibration state value is less than a preset threshold in the preset period of time, obtaining vital sign data by detecting the vital sign of the user located in the smart seat and determining that the user is in the sleeping state or the waking state according to the vital sign data.

When the user is using the smart seat, it is impossible for him to keep moving in the seat all the time even if he is in the waking state, whereas even if the user is in the sleeping state, it is impossible for him to be completely still. Therefore, when it is determined that the user is in the sleeping state or the waking state by the vibration state value, it is necessary to define a range of period of time for the vibration state value, that is, detect the number of vibrations in the preset period of time. After the period of time is determined, the vibration state value on the seating surface 12 is obtained with the preset period of time as the cycle.

A preset threshold of the vibration state value in the preset period of time is preset, to compare the obtained vibration state value with the preset threshold. Exemplarily, the preset period of time is set to be five minutes, and the preset threshold is set to be 2 times. That is, it is considered that for a user using the smart seat of the embodiment of the invention, it is judged that the user may have entered the sleeping state if the number of activities on the seating surface 12 in five minutes is less than 2, and it is judged that the user is still in the waking state at this time if the number of activities on the seating surface 12 in five minutes is greater than or equal to 2.

When the vibration state value is less than the preset threshold in the preset period of time, it is judged that the user may have entered the sleeping state, and at this point, the operations of the steps S101-S102 (obtaining vital sign data by detecting a vital sign of a user located in the smart seat, and determining that the user is in the sleeping state or the waking state according to the vital sign data) are performed.

As such, it may not be necessary to always loop through the steps S101-S102, but only when the vibration state value is less than the preset threshold and it is judged that the user may have entered the sleeping state, the steps S101-S102 are then performed, which increases the operational response speed of the smart seat of the embodiment of the invention at work, and reduces the energy consumption.

Figure 14:
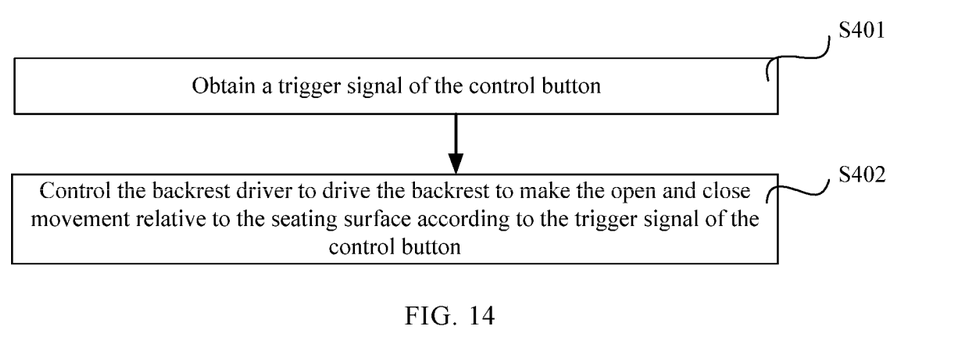
FIG. 14 is a flow chart V of a control method for a smart seat provided by an embodiment of the invention.

Further, as shown in FIG. 9, on the seat body 10 is further arranged a control button 18, and as shown in FIG. 14, the control method further includes:

S401, obtaining a trigger signal of the control button 18.

S402, controlling the backrest driver 13 to drive the backrest 11 to make the open and close movement relative to the seating surface 12 according to the trigger signal of the control button 18.

For example, as shown in FIG. 9, on the seat body 10 are arranged control buttons 18 for performing operations of "open" and "close". When the user triggers the "open" control button 18, according to the trigger signal of the "open" control button 18, the backrest driver 13 is correspondingly controlled to drive the backrest 11 to perform the open operation, to cause the smart seat of the embodiment of the invention to be in the open state. Likewise, when the user triggers the "close" control button 18, according to the trigger signal of the "close" control button 18, the backrest driver 13 is correspondingly controlled to drive the backrest 11 to perform the close operation relative to the seating surface 12, to cause the smart seat of the embodiment of the invention to be in the close state.

In the description of the structure and working process of the smart seat of the embodiment of the invention, the working principles and steps of the smart seat have already been described in detail, which will not be repeated here any longer.

What is described above is just specific embodiments of the invention, however, the protection scope of the invention is not limited thereto, and variations or alternatives easily occurring to any artisan familiar with the technical field within the technical scope disclosed by the invention should be encompassed within the protection scope of the invention. Therefore, the protection scope of the invention should be subject to the protection scope of the claims.

What is claimed is:

1. A smart seat, characterized in that, it includes a seat body, a vital sign detector and a controller,
    the seat body includes a backrest, a seating surface and a backrest driver for driving the backrest to make an open and close movement relative to the seating surface,
    the vital sign detector is used for detecting a vital sign of a user to obtain vital sign data, and
    the controller is electrically connected with the backrest driver and the vital sign detector, respectively, determines that the user is in the sleeping state or the waking state according to the vital sign data of the vital sign detector, and controls the backrest driver to drive the open and close movement of the backrest relative to the seating surface according to the state of the user,
    wherein the vital sign detector is an ultrasonic detector and a processing module, the ultrasonic detector is arranged on the front side of the seat body and sends an ultrasonic signal toward the direction of the seat body and receives a reflected ultrasonic signal, the processing module determines the user's respiratory frequency and/or degree of chest undulation according to the information of the ultrasonic signal received by the ultrasonic detector, and the controller determines that the user is in the sleeping state or the waking state according to the user's respiratory frequency and/or degree of chest undulation,
    wherein on the ultrasonic detector is further arranged an alignment camera which is electrically connected with the controller, on the seat body is further arranged an alignment mark, and the alignment camera is used for capturing an image of the alignment mark, in order that the controller regulates the orientation direction in which the ultrasonic detector sends the ultrasonic signal according to the image of the alignment mark.

2. The smart seat as claimed in claim 1, characterized in that, the backrest is hinged with the seating surface by a side, and the backrest driver drives the backrest to make the open and close movement relative to the seating surface with its hinging side as the axis.

3. The smart seat as claimed in claim 1, characterized in that, the controller controls the backrest to change to the open state in a case in which the controller determines that the user is in the sleeping state according to the vital sign data.

4. The smart seat as claimed in claim 3, characterized in that, it further includes a pressure sensor which is arranged on the seating surface and electrically connected with the controller, and the controller is used for controlling the backrest to be in the close state in a case in which the pressure value born on the seating surface detected by the pressure sensor is less than a preset threshold.

5. The smart seat as claimed in claim 2, characterized in that, the vital sign detector is an ultrasonic detector and a processing module, the ultrasonic detector is arranged on the front side of the seat body and sends an ultrasonic signal toward the direction of the seat body and receives it, the processing module determines the user's respiratory frequency and/or degree of chest undulation according to the information of the ultrasonic signal received by the ultrasonic detector, and the controller determines that the user is in the sleeping state or the waking state according to the user's respiratory frequency and/or degree of chest undulation.

6. The smart seat as claimed in claim 3, characterized in that, the vital sign detector is an ultrasonic detector and a processing module, the ultrasonic detector is arranged on the front side of the seat body and sends an ultrasonic signal toward the direction of the seat body and receives it, the processing module determines the user's respiratory frequency and/or degree of chest undulation according to the information of the ultrasonic signal received by the ultrasonic detector, and the controller determines that the user is in the sleeping state or the waking state according to the user's respiratory frequency and/or degree of chest undulation.

7. The smart seat as claimed in claim 1, characterized in that, the seat body further includes a leg supporting plate hinged with the seating surface by a side of the leg supporting plate and a leg supporting plate driver arranged between the seating surface and the leg supporting plate, and the leg supporting plate driver is electrically connected with the controller and used for driving the leg supporting plate to make an open and close movement relative to the seating surface with its hinging side as the axis under the control of the controller.

8. The smart seat as claimed in claim 2, characterized in that, the seat body further includes a leg supporting plate hinged with the seating surface by a side of the leg supporting plate and a leg supporting plate driver arranged between the seating surface and the leg supporting plate, and the leg supporting plate driver is electrically connected with the controller and used for driving the leg supporting plate to make an open and close movement relative to the seating surface with its hinging side as the axis under the control of the controller.

9. The smart seat as claimed in claim 3, characterized in that, the seat body further includes a leg supporting plate hinged with the seating surface by a side of the leg supporting plate and a leg supporting plate driver arranged between the seating surface and the leg supporting plate, and the leg supporting plate driver is electrically connected with the controller and used for driving the leg supporting plate to make an open and close movement relative to the seating surface with its hinging side as the axis under the control of the controller.

10. The smart seat as claimed in claim 1, characterized in that, on the back of the backrest is further arranged a supporting piece which is retracted on the back of the backrest and parallel to the back and can be opened to support the backrest when the smart seat changes to be in the open state.

11. The smart seat as claimed in claim 1, characterized in that, it further includes at least one vibration sensor, the vibration sensor is arranged on the seating surface and electrically connected with the controller, and the controller is used for driving the vital sign detector to detect a vital sign of the user in a case in which the vibration state value on the seating surface which is detected by the vibration sensor in a preset period of time is less than a preset threshold.

12. The smart seat as claimed in claim 1, characterized in that, on the seat body is further arranged a control button which is electrically connected with the controller and used for controlling the backrest driver to drive the open and close movement of the backrest relative to the seating surface after the control button is triggered.

\* \* \* \* \*